(12) United States Patent
Jacob

(10) Patent No.: US 11,426,307 B2
(45) Date of Patent: Aug. 30, 2022

(54) TREPHINE TO CREATE SHAPED CUTS FOR CORNEA OR TISSUE

(71) Applicant: Soosan Jacob, Chennai (IN)

(72) Inventor: Soosan Jacob, Chennai (IN)

( * ) Notice: Subject to any disclaimer, the term of this patent is extended or adjusted under 35 U.S.C. 154(b) by 374 days.

(21) Appl. No.: 16/480,474

(22) PCT Filed: May 1, 2018

(86) PCT No.: PCT/IN2018/000025
§ 371 (c)(1),
(2) Date: Jul. 24, 2019

(87) PCT Pub. No.: WO2018/203341
PCT Pub. Date: Nov. 8, 2018

(65) Prior Publication Data
US 2019/0380868 A1    Dec. 19, 2019

(30) Foreign Application Priority Data

May 4, 2017   (IN) .............................. 201741015789

(51) Int. Cl.
*A61F 9/007*    (2006.01)
*A61F 9/013*    (2006.01)

(52) U.S. Cl.
CPC ............ *A61F 9/007* (2013.01); *A61F 9/0133* (2013.01)

(58) Field of Classification Search
CPC ........ A61F 9/007; A61F 9/0133; A61F 9/013; A61F 9/00736; A61F 9/00745; A61F 9/00754; A61F 9/00763; A61B 17/32
See application file for complete search history.

(56) References Cited

U.S. PATENT DOCUMENTS 4,190,050 A    2/1980  Bailey
4,526,171 A *  7/1985  Schachar ................ A61F 9/013
                                                   606/166

(Continued)

*Primary Examiner* — Kelly J Bekker
*Assistant Examiner* — Andrew P. Restaino
(74) *Attorney, Agent, or Firm* — Law Offices of Steven W. Weinrieb

(57) ABSTRACT

The shaped corneal/other tissue/bioengineered material trephines can create single or combination of shaped cuts and sections in cornea, sclera or any other tissue or bioengineered material of desired shapes, thickness, width, depth, radius, sizes/dimensions, measurements and configurations. It can create certain patterned or shaped cuts in tissue including but not limited to cornea and sclera/bioengineered material without using the femtosecond laser, especially in the case of cornea where at present the femtosecond laser is required for this purpose. A manual or motorized trephine allows creating cuts in different shapes, thicknesses, width, depth, radius, sizes/dimensions, configurations and measurements with single/multiple or combination of cuts. These configurable cuts give the advantage of creating shaped incisions/sections in the body of a subject as well as give the ability to create donor and recipient sections of cornea, sclera or any other tissue or bioengineered material of specific shapes and dimensions. It therefore gives the ability to create these shaped cuts and sections of tissue without the need for a femtosecond laser and also ability to cut through tissue that is not necessarily transparent.

14 Claims, 9 Drawing Sheets

(56) References Cited

U.S. PATENT DOCUMENTS

| | | | | |
|---|---|---|---|---|
| 4,796,623 A * | 1/1989 | Krasner | ............ | A61F 9/013 |
| | | | | 600/565 |
| 6,036,709 A * | 3/2000 | Boutros | ............ | A61F 9/013 |
| | | | | 606/166 |
| 6,565,584 B1 * | 5/2003 | Mathis | ............ | A61F 2/147 |
| | | | | 128/898 |
| 2006/0287663 A1 * | 12/2006 | Gayheart | ............ | A61F 9/0133 |
| | | | | 606/166 |

* cited by examiner

TREPHINE TO CREATE SHAPED CUTS FOR CORNEA OR TISSUE

FIELD OF THE INVENTION

The field of this invention refers to a device used in surgery on the human eye/any other tissue, in cases where specifically shaped or separated single or multiple cuts, eg corneal cuts are required. More specifically, the present invention relates to a manual or motorized trephine used to cut tissue including but not limited to the cornea or sclera, either in the subject or in the donor corneo-scleral button or other tissue or bioengineered material, where a combination of blades allows the cornea/tissue to be cut in a specific manner or shape.

BACKGROUND OF THE INVENTION

There are numerous conditions of the eye or other part of the body which require placement of donor grafts that are of a particular shape, size or particular thickness. There are also conditions where cuts or incisions may be desired in a particular shape, size or configuration in the subject's body including but not confined to the human eye. Some examples of these are the need to create ring shaped tissue of different thicknesses or width, to create long segments of tissue of different thicknesses or width, to cut tissue in a top hat configuration or a mushroom shaped configuration; to create oval, square or crescentic or any other shaped tissue in the donor graft or alternatively to prepare the recipient tissue or the subject's tissue in these above mentioned or other possible shapes and configurations. These are often especially required in the subject's cornea or sclera but may also be required in other tissues. To overcome this problem, the femtosecond laser may be used to program and create shaped cuts within the tissue. However this has the disadvantages of having the need for a femtosecond laser, being very expensive and also not being able to create cuts through scarred or opaque tissue as the femtosecond laser needs light passage through the tissue it cuts and therefore can be used only in optically clear or transparent tissue.

There is therefore a recognized need in the art for an improved device which can create these shaped corneal/other tissue cuts without the need for a femtosecond laser and also which can cut through tissue that is not necessarily transparent. The present invention fulfills this long standing need in the art.

SUMMARY OF THE INVENTION

The invention relates to surgical instruments and more specifically to trephining instruments that can create single or combination of cuts in human/other tissue or bioengineered material of desired shapes, sizes and configurations. An object of the present invention is to have a means of being able to create certain patterned or shaped cuts in tissue.

A manual or motorized trephine which allows creating cuts in different shapes, thickness, width, depth, radius, sizes/dimensions, measurements and configurations with single or combination of cuts. These configurable cuts will give the advantage of creating shaped incisions in the body of a subject (especially on the cornea and sclera but not limited to it), as well as give the ability to create donor or recipient sections of tissue of specific shapes and dimensions.

Ability to create these shaped cuts and sections of cornea/sclera/other tissue without the need for a femtosecond laser and also ability to cut through tissue that is not necessarily transparent are advantages of this device.

BRIEF DESCRIPTION OF THE DRAWINGS

Referring now to the drawings wherein the showings are for the purpose of illustrating preferred embodiment of the inventions only, and not for the purpose of limiting the same.

The longitudinal section of the double blades of the trephine is shown (d). Different parts are labelled (a-outer blade; b-inner blade). The cut obtained in the tissue placed convex up is shown (e). The cut obtained in the tissue placed concave up is shown (f).

Figure 1A:
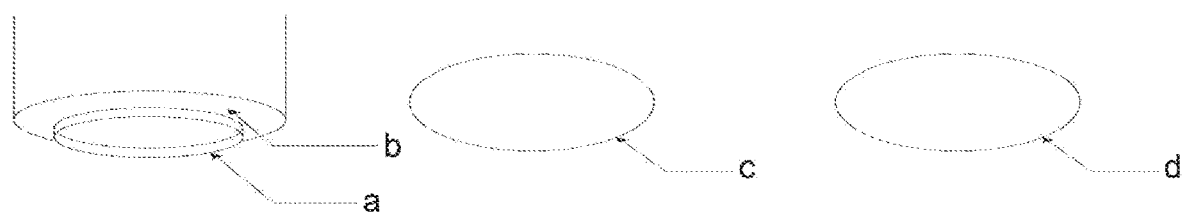
FIG. 1A: The design of an oval trephine is shown. Different parts are labelled. (a-blade; b-holder). The oval cross section of the trephine blade is shown (c). The oval shape of the tissue that is cut is shown (d).
Figure 1B:
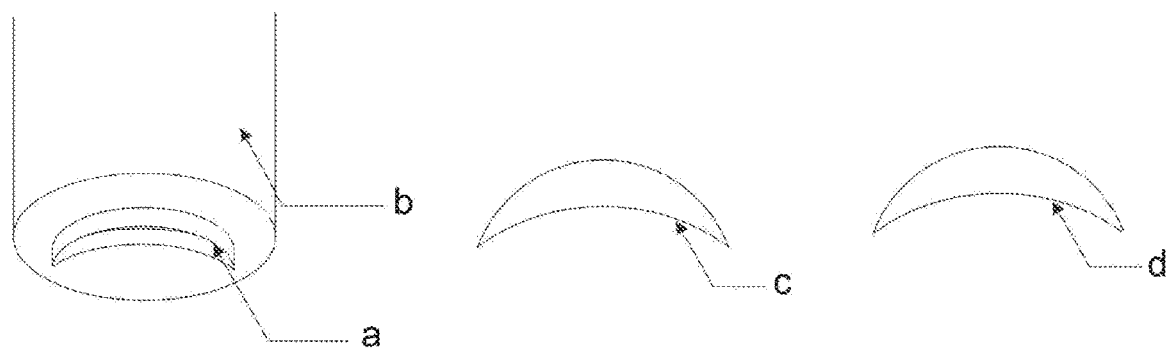
FIG. 1B: The design of a crescentic trephine is shown. Different parts are labelled. (a-blade; b-holder). The crescentic cross section of the trephine blade is shown (c). The crescentic shape of the tissue that is cut is shown (d).
Figure 1C:
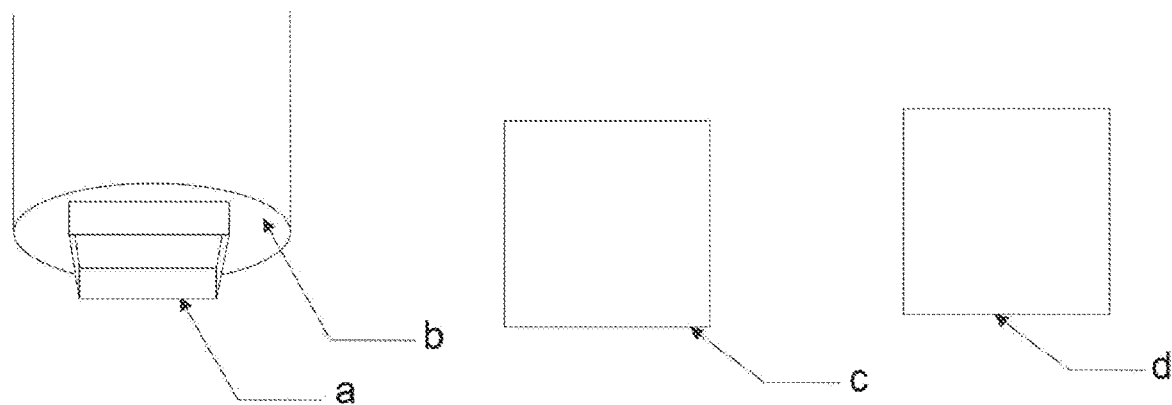
FIG. 1C: The design of a square trephine is shown. Different parts are labelled. (a-blade; b-holder). The square cross section of the trephine blade is shown (c). The square shape of the tissue that is cut is shown (d).
Figure 1D:
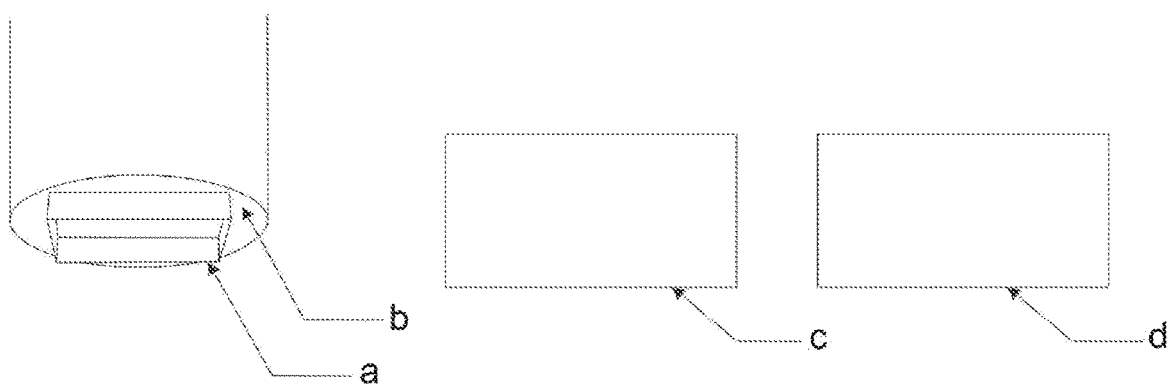
FIG. 1D: The design of a rectangular trephine is shown. Different parts are labelled. (a-blade; b-holder). The rectangular cross section of the trephine blade is shown (c). The rectangular shape of the tissue that is cut is shown (d).
Figure 1E:
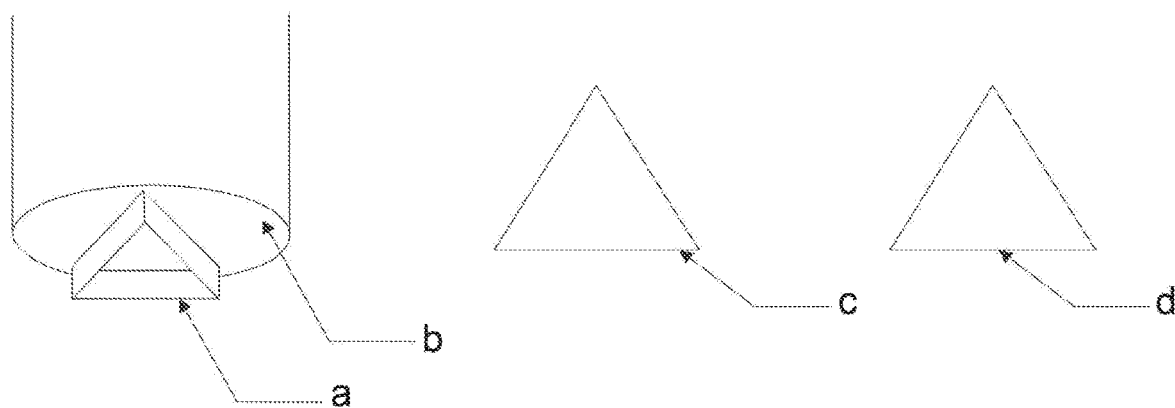
FIG. 1E: The design of a triangular trephine is shown. Different parts are labelled. (a-blade; b-holder). The triangular cross section of the trephine blade is shown (c). The triangular shape of the tissue that is cut is shown (d).
Figure 1F:
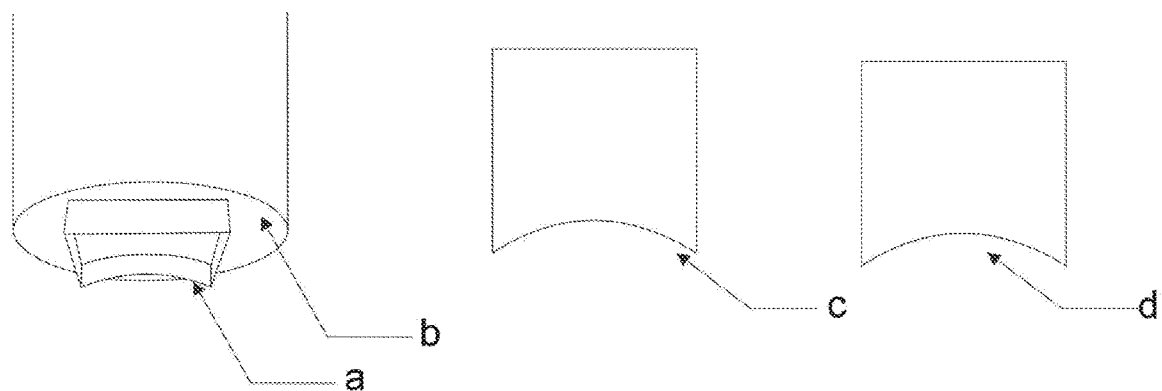
FIG. 1F: The design of circular one side corners rectangle trephine is shown. Different parts are labelled. (a-blade; b-holder). The circular one side corners rectangle cross section of the trephine blade is shown (c). The circular one side corners rectangle shape of the tissue that is cut is shown (d).
Figure 1G:
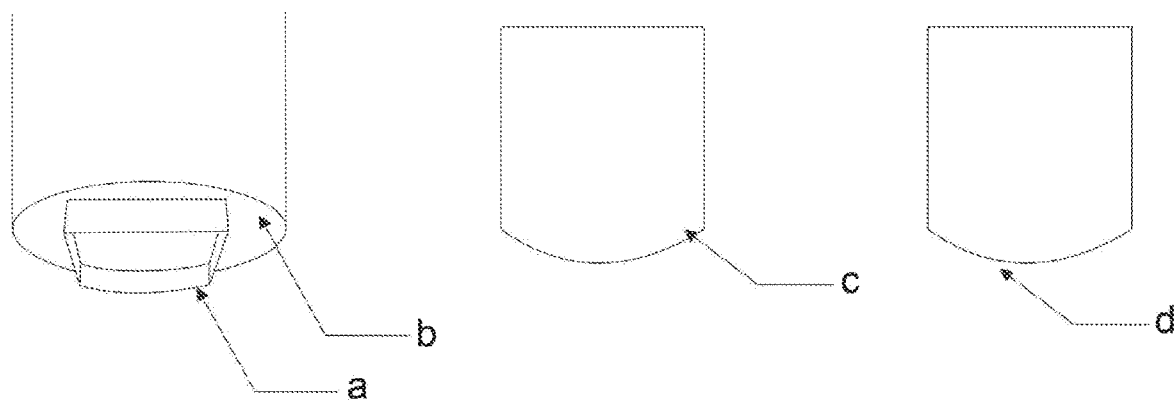
FIG. 1G: Another design of circular one side corners rectangle trephine is shown. Different parts are labelled. (a-blade; b-holder). The circular one side corners rectangle cross section of the trephine blade is shown (c). The circular one side corners rectangle shape of the tissue that is cut is shown (d).
Figure 2:
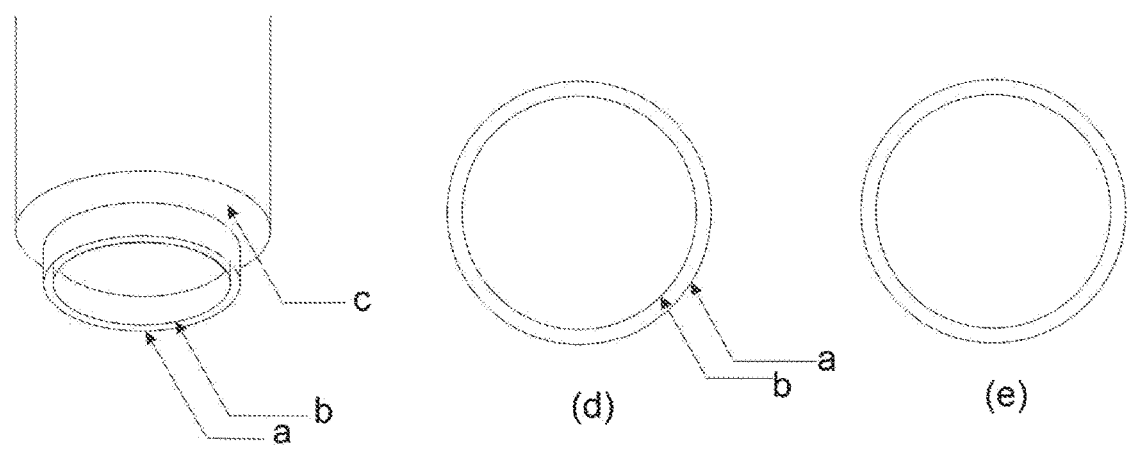
FIG. 2: The design of same level double bladed trephine is shown. Different parts are labelled. (a-outer blade; b-inner blade, c-holder). The cross section of the double blades of the trephine is shown (d). Different parts are labelled (a-outer blade; b-inner blade). The ring shaped tissue that is cut is shown (e).
Figure 3:
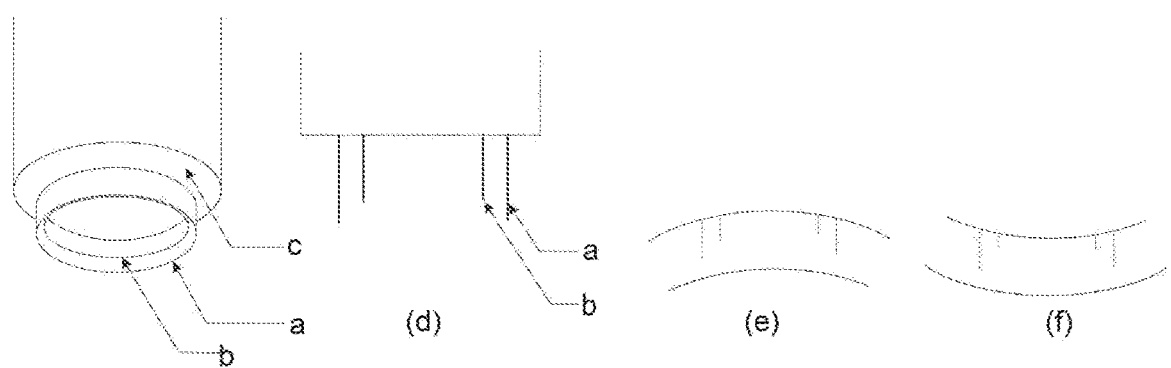
FIG. 3: The design of tophat shaped stepped level double bladed trephine is shown. Different parts are labelled. (a-outer blade; b-inner blade, c-holder). The longitudinal section of the double blades of the trephine is shown (d). Different parts are labelled (a-outer blade; b-inner blade). The cut obtained in the tissue placed convex up is shown (e). The cut obtained in the tissue placed concave up is shown (f).
Figure 4:
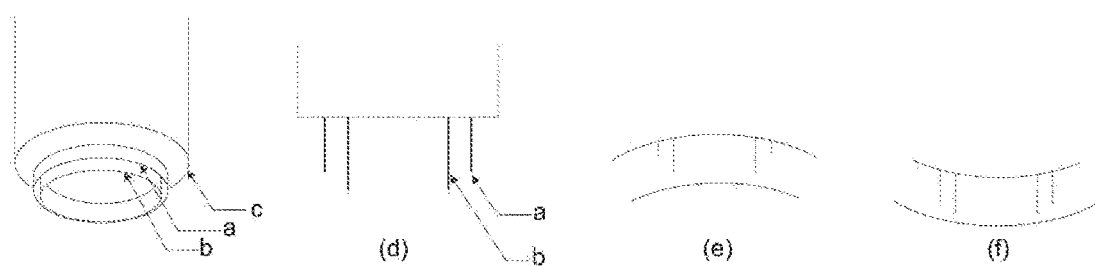
FIG. 4: The design of a mushroom stepped level double bladed trephine is shown. Different parts are labelled. (a-outer blade; b-inner blade, c-holder). The longitudinal section of the double blades of the trephine is shown (d). Different parts are labelled (a-outer blade; b-inner blade). The cut obtained in the tissue placed convex up is shown (e). The cut obtained in the tissue placed concave up is shown (f).
Figure 5A:
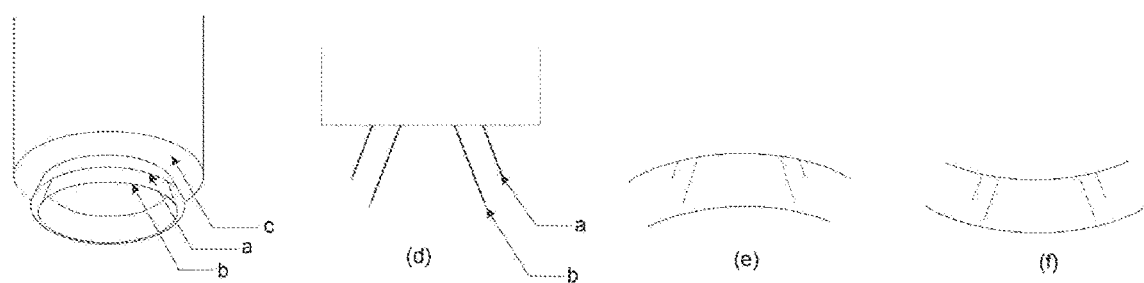
FIG. 5A: Design of zig zag (Christmas tree) shaped stepped level double bladed trephine is shown Different parts are labelled. (a-outer blade; b-inner blade, c-holder).
Figure 5B:
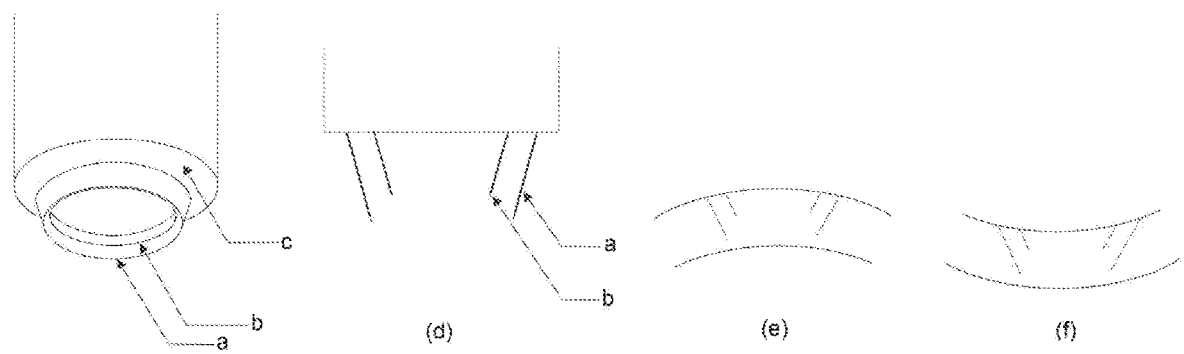

FIG. 5B: Design of zig zag (inverted Christmas tree) shaped stepped level double bladed trephine is shown Different parts are labelled. (a-outer blade; b-inner blade, c-holder). The longitudinal section of the double blades of the trephine is shown (d). Different parts are labelled (a-outer blade; b-inner blade). The cut obtained in the tissue placed convex up is shown (e). The cut obtained in the tissue placed concave up is shown (f).

Figure 6:
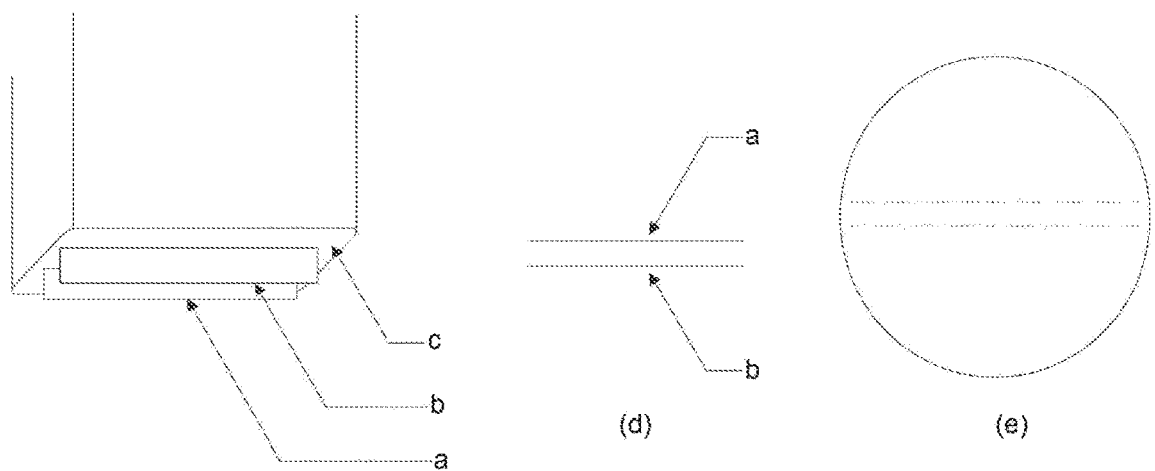

FIG. 6: The design of straight same level parallel trephine is shown. Different parts are labelled. (a-first blade; b-second blade; c-holder). The cross section of the double blades of the trephine is shown (d). Different parts are labelled (a-first blade; b-second blade). The straight segment of tissue that is cut is shown (e).

Figure 7:
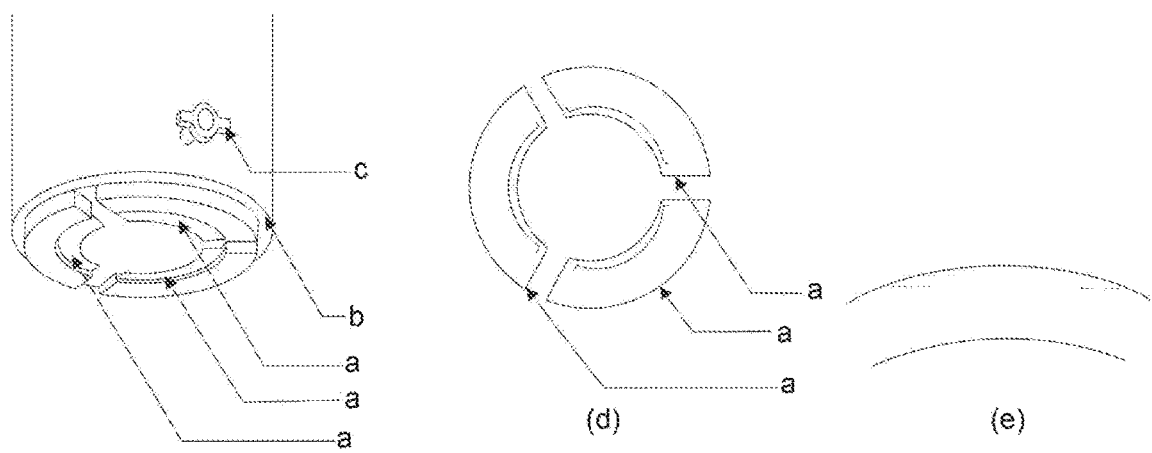

FIG. 7: The design of an inward cutting horizontal trephine is shown. Different parts are labelled (a-horizontal blades, b-holder, c-adjustable moving device). The cross section of the blades of the trephine is shown (d). The horizontal blades are labelled (a). The cutting edge of the blade is depicted as double lined. The cut obtained in the tissue is shown in dotted lines (e).

Figure 8:
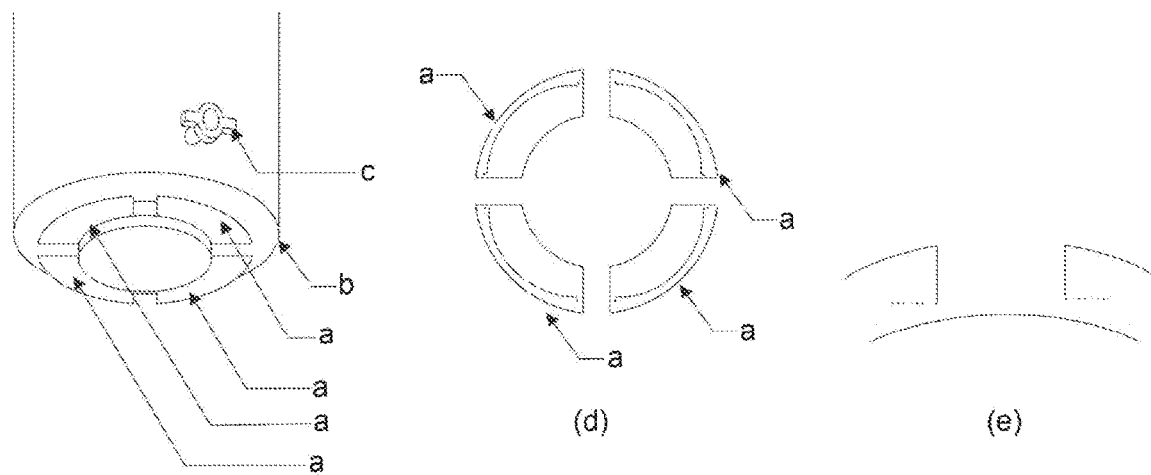

FIG. 8: The design of an outward cutting horizontal trephine is shown. Different parts are labelled (a-horizontal blades, b-holder, c-adjustable moving device). The cross section of the blades of the trephine is shown (d). The horizontal blades are labelled (a). The cutting edge of the blade is depicted as double lined. The cut obtained in the tissue is shown in dotted lines (e).

Figure 9:
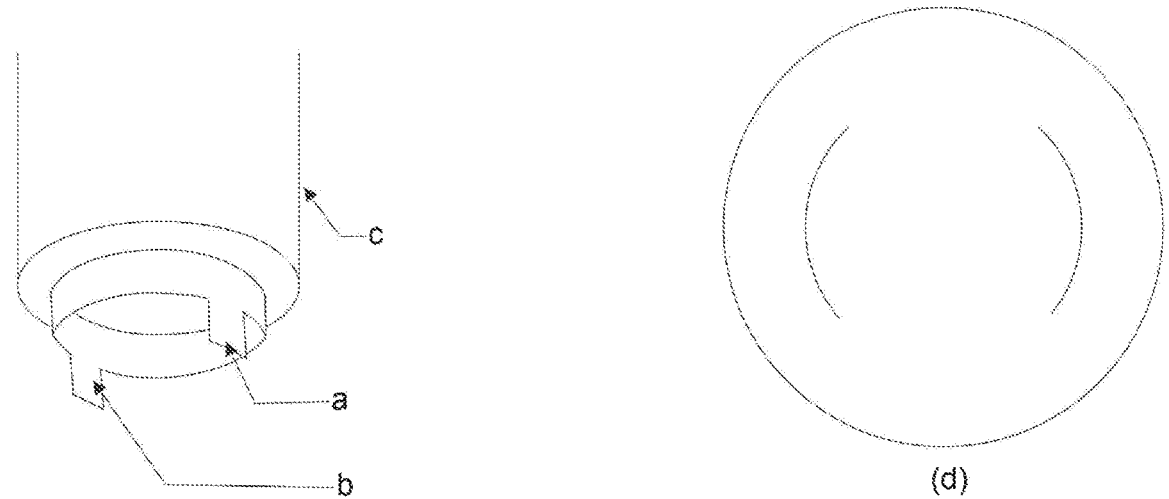

FIG. 9: The design of a segmented blade trephine is shown. Different parts are labelled. (a-first segment; b-second segment, c-holder): The segmental incision made on the tissue that is cut is shown (d).

Figure 10:
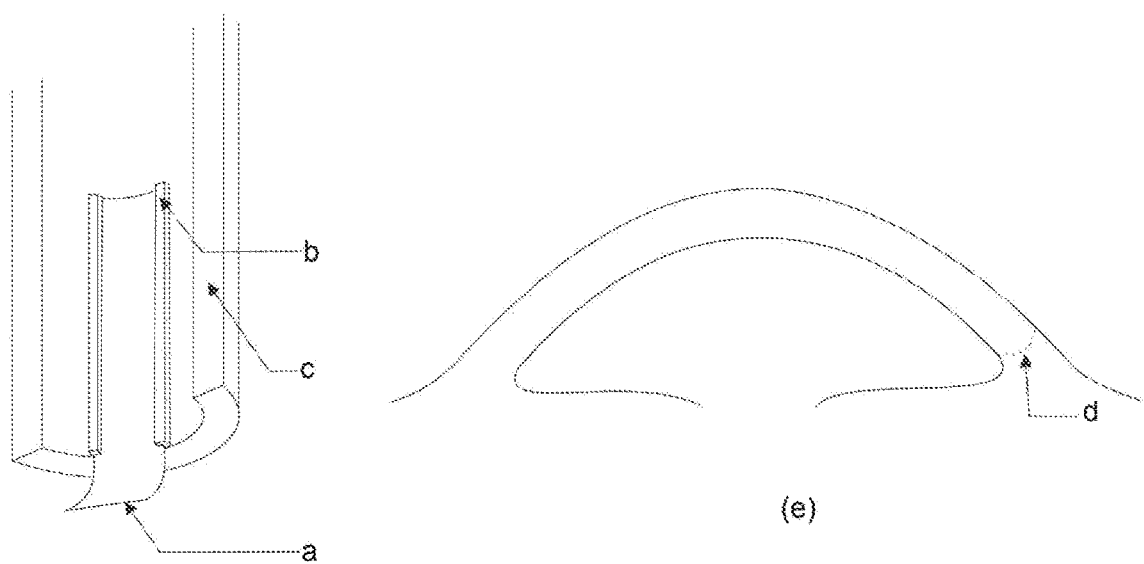

FIG. 10: The design of a curved blade trephine is shown. Different parts are labelled. (a-curved blade; b-channel for blade to move in; c-holder). The segmental incision (d) made on the tissue that is cut is shown (e). Other cuts may also be possible by different paths and angulations for the blade.

DETAILED DESCRIPTION OF THE INVENTION

"tissue" as mentioned herein 'cornea, sclera or any other tissue or bioengineered material that is cut with any of the devices described herein'.

The present invention will be described herein below with reference to the accompanying drawings. The present invention provides the ability to create shaped cuts and sections of tissue in different shapes, thickness, width, depth; radius, sizes/dimensions, measurements and configurations with single or combination of cuts without the need for a femtosecond laser and also ability to cut through tissue that is not necessarily transparent. These configurable cuts gives the advantage of creating shaped incisions in the body of a subject as well as gives the ability to create donor or recipient sections of tissue or bioengineered material of specific shapes and dimensions.

Embodiment 1: Shaped Trephine

The trephine has blades that are capable of cutting an oval, crescentic, square, rectangular, triangular, circular one side corners rectangle or other predefined shapes as desired. The tissue may be cut either mechanically in the form of open trephine or a suction based apparatus or by a motorized apparatus. The size/depth/other dimension is adjustable by adjusting the blade configuration. The tissue cut may be corneal, scleral or any other tissue or bioengineered material. There may be further parts in the device to ensure proper placement and centration.

Embodiment 2: Same Level Double Bladed Trephine

The trephine has inner and outer blades at the same level that are capable of cutting a round, oval, crescentic, square, rectangular, triangular, circular one side corners rectangle or other predefined shapes as desired. The tissue may be cut either mechanically in the form of open trephine or a suction based or other apparatus or by a motorized apparatus. The size/depth/other dimension is adjustable by adjusting the blade configuration. Multiple concentric blades may also be placed within each other to create shaped segments of tissue. The tissue cut may be corneal, scleral or any other tissue or bioengineered material. There may be further parts in the device to ensure proper placement and centration.

Embodiment 3: Stepped Level Perpendicular Double Bladed Trephine

The trephine has perpendicular inner and outer blades at two levels that are capable of creating round, oval, crescentic, square, rectangular, triangular, circular one side corners rectangle or other predefined shapes as desired. One of the cuts extends only through partial thickness of the cornea and the second cut may be set to extend through full thickness or partial thickness of the cornea. The two cuts thus created may be joined if desired either by a horizontal cutting trephine or manually with a dissector or a microscissor. The cuts may be made either mechanically in the form of open trephine or a suction based or other apparatus or by a motorized apparatus. The size/depth/other dimension is adjustable by adjusting the blade configuration. These trephines may be used to obtain cuts that can finally give a tophat or mushroom or other specific shaped cuts. The tissue cut may be corneal, scleral or any other tissue or bioengineered material. There may be further parts in the device to ensure proper placement and centration.

Embodiment 4: Stepped Level Slanting Double Bladed Trephine

The trephine has slanting inner and outer blades at two levels that are capable of creating round, oval, crescentic, square, rectangular, triangular, circular one side corners rectangle or other predefined shapes as desired. One of the cuts extends only through partial thickness of the cornea and the: second cut may be set to extend through full thickness or partial thickness of the cornea. The two cuts thus created may be joined if desired either by a horizontal cutting trephine or manually with a dissector or a microscissor. The cuts may be made either mechanically in the form of open trephine or a suction, based or other apparatus or by a motorized apparatus. The size/depth/other dimension is adjustable by adjusting the blade configuration. These trephines may be used to obtain cuts that can finally give a zigzag or other specific shaped cuts. The tissue cut may be corneal, scleral or any other tissue or bioengineered mate-

Embodiment 5: Same Level Parallel Double Bladed Trephine

The trephine has straight parallel blades at the same level that are capable of cutting a straight segment of tissue. The tissue may be cut either mechanically in the form of open trephine or a suction based or other apparatus or by a motorized apparatus. The size/depth/other dimension is adjustable by adjusting the blade configuration. Multiple parallel blades may also be placed next to each other to create multiple segments of tissue. The tissue cut may be corneal, scleral or any other tissue or bioengineered material. There may be further parts in the device to ensure proper placement and centration.

Embodiment 6: Horizontal Trephine

The trephine has inward or outward cutting horizontal blades placed in a circular manner that are capable of creating horizontal cuts: The cuts may be made either mechanically in the form of open trephine or a suction based or other apparatus or by a motorized apparatus. The size/depth/other dimension is adjustable by adjusting the blade configuration. The tissue cut may be corneal, scleral or any other tissue or bioengineered material. There may be further parts in the device to ensure proper placement and centration.

Embodiment 7: Segmented Blade Trephine

The trephine has segmented blades in two or more sectors that are capable of creating segmented cuts in tissue with clear gaps or uncut areas of tissue in between. These may be made as circular or as oval, crescentic, square, rectangular, triangular, circular one side corners rectangle or other predefined shapes as desired. They may extend only through partial thickness of the tissue or through full thickness. The cuts may be made either mechanically in the form of open trephine or a suction based or other apparatus or by a motorized apparatus. The size/depth/other dimension is adjustable by adjusting the blade configuration. The tissue cut may be corneal, scleral or any other tissue or bioengineered material and may be capable of creating incisions such as limbal relaxing incisions etc. There may be further parts in the device to ensure proper placement and centration.

Embodiment 8: Special Trephines

The trephine may slide along angled or curved channels/surfaces to create shaped clear corneal or other incisions of predefined/preset dimensions.

Embodiment 9: Combination Trephines

The cuts previously described in other embodiments may be used in combination, eg. vertical cuts in combination with horizontal cuts or other combinations of any size/depth/other dimension.

The foregoing description is for a few embodiments of the present invention. It should be appreciated that these embodiments are described for purpose of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Other modifications will be apparent to those skilled in the art and, therefore, the invention is defined in the claims.

What is claimed is:

1. A trephine assembly for forming specifically configured corneal pieces that are required in connection with different types of corneal surgery, comprising:
    a blade holder defined around a longitudinal axis; and a pair of non-serrated cutting blades mounted upon said blade holder and disposed concentrically with respect to each other so as to be spaced from each other by a predetermined distance such that said pair of non-serrated blades sever a slice of tissue from an organism wherein the width of the tissue severed from the organism has a width corresponding to said predetermined distance that said pair of non-serrated cutting blades are spaced from each other;
    wherein said pair of non-serrated cutting blades disposed concentrically with respect to each other have different depth dimensions as measured from said blade holder such that specifically configured corneal pieces can be obtained as required in connection with different types of corneal surgery.

2. The trephine assembly as set forth in claim 1, wherein:
    said pair of non-serrated cutting blades comprise circular blades disposed concentrically with respect to each other such that the tissue severed from the organism has an annular configuration.

3. The trephine assembly as set forth in claim 1, wherein:
    an inner one of said pair of non-serrated cutting blades, disposed concentrically with respect to each other, has a greater depth than an outer one of said pair of non-serrated cutting blades disposed concentrically with respect to each other.

4. The trephine assembly as set forth in claim 1, wherein:
    an outer one of said pair of non-serrated cutting blades, disposed concentrically with respect to each other, has a greater depth than an inner one of said pair of non-serrated cutting blades disposed concentrically with respect to each other.

5. The trephine assembly as set forth in claim 2, wherein:
    said blade holder has a mounting surface upon which said pair of non-serrated cutting blades are mounted and from which said pair of non-serrated cutting blades extend such that said mounting surface is disposed perpendicular to said longitudinal axis; and
    said pair of non-serrated cutting blades extend outwardly from said mounting surface of said blade holder such that diametrically opposite portions of each one of said pair of non-serrated cutting blades extends at a predetermined angle with respect to said mounting surface of said blade holder and with respect to said longitudinal axis of said blade holder.

6. The trephine assembly as set forth in claim 5, wherein:
    said pair of non-serrated cutting blades extend outwardly from said mounting surface of said blade holder such that diametrically opposite portions of said pair of non-serrated cutting blades extend parallel to a plane within which said longitudinal axis of said blade holder is disposed and perpendicular to said mounting surface of said blade holder.

7. The trephine assembly as set forth in claim 5, wherein:
    said pair of non-serrated cutting blades extend outwardly from said mounting surface of said blade holder such that diametrically opposite portions of said pair of non-serrated cutting blades extend at a predetermined acute angle with respect to a plane within which said longitudinal axis of said blade holder is disposed such that said diametrically opposite portions of said pair of non-serrated cutting blades are angled toward each other.

8. The trephine assembly as set forth in claim 5, wherein:
said pair of non-serrated cutting blades extend outwardly from said mounting surface of said blade holder such that diametrically opposite portions of said pair of non-serrated cutting blades extend at a predetermined acute angle with respect to a plane within which said longitudinal axis of said blade holder is disposed such that said diametrically opposite portions of said pair of non-serrated cutting blades are angled away each other.

9. An ocular blade assembly for forming specifically configured corneal pieces that are required in connection with different types of corneal surgery, comprising:
a blade holder defined around a longitudinal axis and including a bottom support surface; and
a pair of linear cutting blades, wherein each one of said linear cutting blades has a substantially rectangular configuration, is mounted upon said blade holder so as to extend below said bottom support surface of said blade holder and disposed substantially parallel with respect to each other so as to be spaced from each other by a predetermined distance such that said pair of blades sever a slice of tissue from an organism wherein the width of the tissue severed from the organism has a width corresponding to said predetermined distance that said pair of blades are spaced from each other.

10. The ocular blade assembly as set forth in claim 9, wherein:
said pair of linear blades are disposed parallel with respect to each other such that the tissue severed from the organism has a substantially rectangular configuration.

11. The ocular blade assembly as set forth in claim 9, wherein:
said pair of linear cutting blades are mounted upon said bottom support surface and extend from said bottom support surface, the bottom support surface has a longitudinal axis around which said bottom support surface is defined such that said bottom support surface is disposed perpendicular to said longitudinal axis of said blade holder; and
said pair of linear cutting blades extend outwardly from said bottom support surface of said blade holder at a predetermined angle with respect to said bottom support surface of said blade holder.

12. The ocular blade assembly as set forth in claim 11, wherein:
said pair of linear cutting blades extend outwardly from said bottom support surface of said blade holder so as to extend parallel to a plane within which said longitudinal axis of said blade holder is disposed and perpendicular to said bottom support surface of said blade holder.

13. A trephine assembly for forming specifically configured corneal pieces that are required in connection with different types of corneal surgery, comprising:
a blade holder defined around a longitudinal axis and having a mounting surface disposed with a plane perpendicular to said longitudinal axis of said blade holder;
a plurality of arcuately shaped bodies mounted upon said mounting surface of said blade holder so as to be disposed within planes that are substantially parallel to said plane within which said mounting surface of said blade holder is disposed, wherein said plurality of arcuately shaped bodies are circumferentially spaced from each other, wherein each one of said plurality of arcuately shaped bodies comprises a pair of arcuately shaped cutting blades disposed perpendicular to said plane within which said mounting surface of said blade holder is disposed, and wherein said pair of arcuately shaped cutting blades are substantially concentric with respect to each other so as to be spaced from each other by a predetermined radial distance such that said pair of blades sever a slice of tissue from an organism wherein the width of the tissue severed from the organism has a width dimension corresponding to said predetermined radial distance that said pair of blades are spaced from each other; and
an oscillator for oscillating said blade holder in opposite arcuate directions around said longitudinal axis of said blade holder such that said pairs of arcuately shaped cutting blades cut arcuate incisions within a tissue of an organism.

14. The trephine assembly as set forth in claim 13, wherein:
said oscillator oscillates said blade holder through different angular distances such that the length of said arcuate incisions cut into the tissue of the organism by said pairs of arcuately shaped cutting blades depends upon the extent to which said blade holder is oscillated by said oscillator.

* * * * *